United States Patent [19]
Gilliland et al.

[11] 3,938,523
[45] Feb. 17, 1976

[54] PREFOLDED AND PACKAGED DISPOSABLE DIAPER

[75] Inventors: Barbara Faye Gilliland, Blackwood, N.J.; Christine Arentzen Henisee, West Chester, Pa.

[73] Assignee: Scott Paper Company, Philadelphia, Pa.

[22] Filed: Oct. 17, 1974

[21] Appl. No.: 515,699

[52] U.S. Cl. .............................. 128/287; 128/284
[51] Int. Cl.$^2$ .................. A61F 13/14; A41B 13/02
[58] Field of Search ................ 128/284, 287, 290 R

[56] References Cited
UNITED STATES PATENTS

| | | | |
|---|---|---|---|
| 1,994,135 | 2/1935 | Horowitz | 128/284 |
| 2,494,933 | 1/1950 | Donahue | 128/284 |
| 3,605,746 | 9/1971 | Schaar | 128/284 |
| 3,710,797 | 1/1973 | Marsan | 128/284 |
| 3,776,233 | 12/1973 | Schaar | 128/287 |
| 3,794,033 | 2/1974 | Ryan | 128/284 |
| R26,515 | 1/1969 | Holliday et al. | 128/284 |

Primary Examiner—Aldrich F. Medbery
Attorney, Agent, or Firm—Martin L. Faigus; William J. Foley

[57] ABSTRACT

A substantially rectangular disposable diaper having a longitudinal dimension defined between end margins and a shorter transverse dimension defined between side margins is prefolded and packaged in a unique configuration including a double-pleat fold on each side of the diaper. Each double-pleat fold includes an inner panel overlying a central section of the diaper and an outer panel overlying the inner panel. Each outer panel includes two wing sections; one on each side of a transversely extending medial line of the diaper. Therefore, the four wing sections of both outer panels are disposed in pairs of two; one pair being on each side of the transversely extending medial line. The two wing sections which are on the same side of the medial line diverge from each other in a direction from the medial line to an end margin of the diaper. The double-pleat folded diaper is folded along the transversely extending medial line to complete the prefolded configuration in which the diaper is packaged.

5 Claims, 4 Drawing Figures

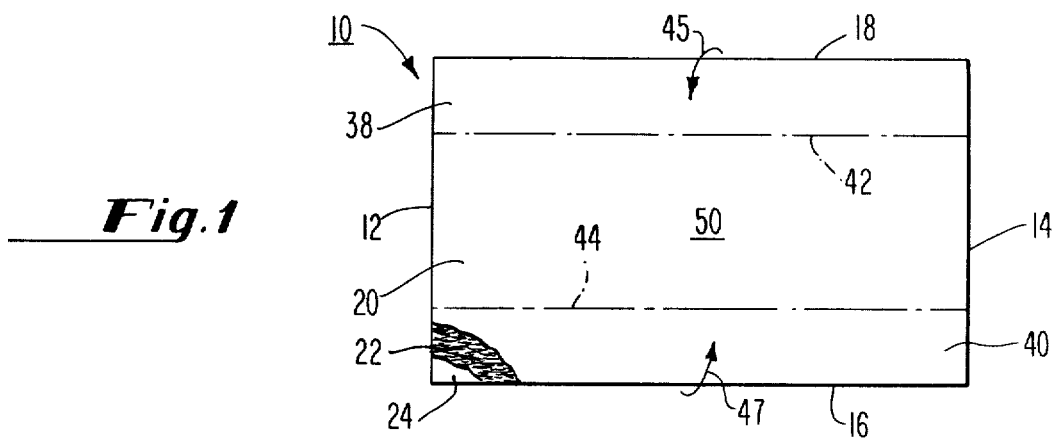
_Fig. 1_
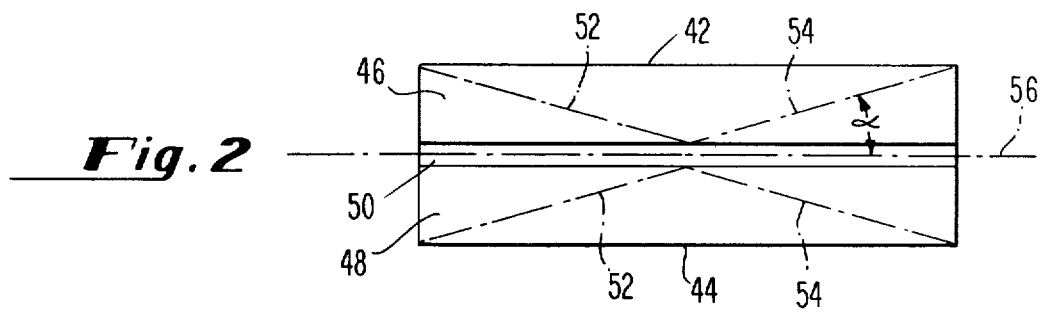
_Fig. 2_
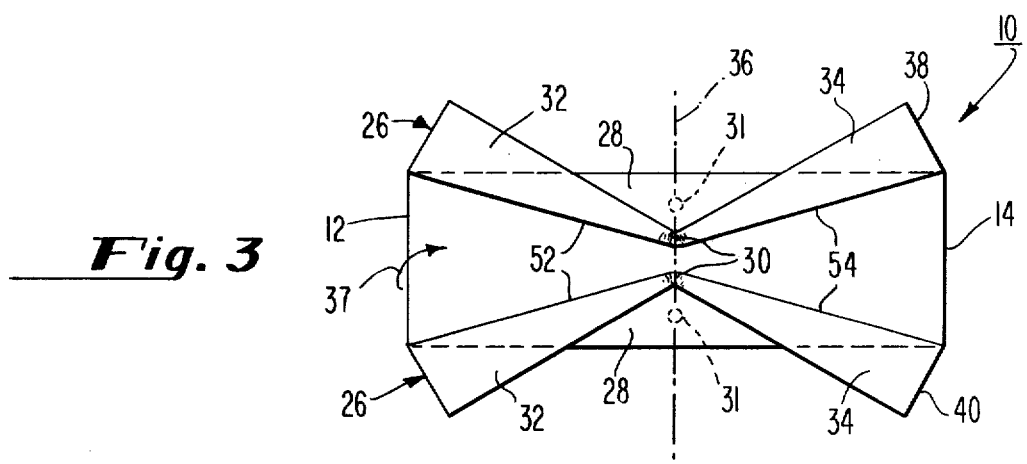
_Fig. 3_
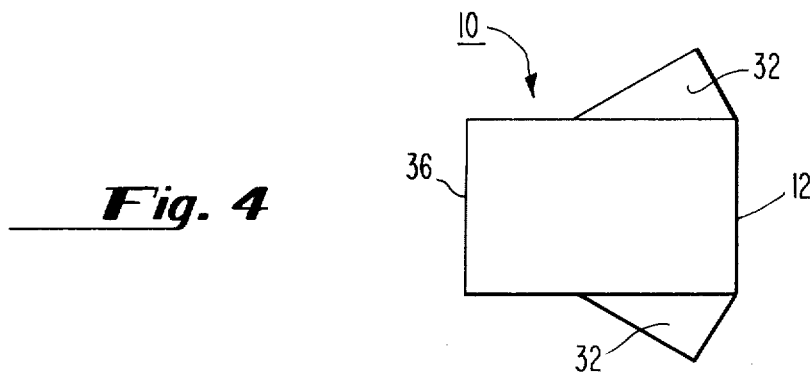
_Fig. 4_

PREFOLDED AND PACKAGED DISPOSABLE
DIAPER

BACKGROUND OF THE INVENTION

1. Field of the Invention

This invention relates to an improvement in prefolded and packaged disposable diapers, and more specifically to a disposable diaper having a prefolded and packaged configuration which clearly indicates the proper manner of placing the diaper on a wearer.

2. Description of Prior Art

Prefolded and packaged disposable diapers are known in the prior art, as evidenced by the disclosures in U.S. Pat. Nos. Re 26,151, issued to Duncan et al; 3,426,756, issued to Romanek and 3,196,874, issued to Hrubecky.

U.S. Pat. Nos. Re 26,151 and 3,426,756 disclose disposable diapers having double-pleat folds at opposite sides thereof. Each double-pleat fold includes an inner panel and an outer panel, both of which are substantially rectangular when the diaper is packaged. The double-pleat folded diaper is folded in half along a transversely extending medial line into a substantially rectangular, or square configuration in which it is packaged for sale. In use the double-pleat folds should be left intact in the perineal region because they are intended to function as a dam when placed on a wearer to aid in retaining body fluids within the confines of the diaper. However, in many cases, a user, that is, a person diapering a wearer, completely opens the double-pleat folds prior to placing the diaper on a wearer because the square or rectangular prefolded construction of the diaper does not provide a clear, visible indication to the user that the folds should be left intact.

U.S. Pat. No. 3,196,874 discloses a diaper in which the sides are prefolded along lines intersecting the side margins of the diaper. The diaper is also prefolded along its transversely extending medial line, and thereby assumes a triangular-shaped configuraton simulating the configuration which should be maintained when the diaper is placed on a wearer. To further explain, when a diaper is placed on a wearer the medial region of the diaper is narrow because it is confined between the wearer's thighs in the perineal region, and the diaper widens toward the opposed ends thereof which encircle the front and back of the wearer. Thus, the triangular-shaped configuration simulates these dimensional relationships to visibly indicate that the side folds should be left intact when the diaper is placed on a wearer. However, when the diaper is unfolded along the transversely extending medial line for placement on a wearer the side folds may open up, even if tacked, and may not assume the desired folded configuration on the wearer without the aid of some manipulation of the diaper by the user. This manipulation may require considerable manual dexterity, especially when the user is placing the diaper upon a particularly active wearer, such as a young child. Additionally, the prefolded construction disclosed in this patent is somewhat complex, and requires fairly sophisticated converting equipment for forming the folds.

SUMMARY OF THE INVENTION

In accordance with this invention a substantially rectangular diaper is prefolded and packaged in a unique configuration including a double-pleat fold on each side of the diaper. Each double-pleat fold includes an inner panel overlying a central section of the diaper, and an outer panel overlying the inner panel. The outer panel of each double-pleat fold includes two wing sections; one on each side of a transversely extending medial line of the diaper. Accordingly, the four wing sections of both outer panels are disposed in pairs of two; one pair being on each side of the transversely extending medial line. The two wing sections which are on the same side of the medial line diverge from each other in a direction from the medial line to an end margin of the diaper. The fold construction is completed by folding the diaper in half along the transversely extending medial line, and the diaper is packaged in this configuration.

The prefolded and packaged diaper of this invention has a flared configuration in plan view. More specifically, the diaper flares outwardly in a direction from the transversely extending medial fold line to the end margins of the diaper. This flared configuraton approximates the shape the diaper assumes when placed on a wearer, and thereby provides a visible indication to a person placing the diaper on a wearer that the double-pleat folds should be left intact in the perineal region when the diaper is placed on a wearer.

BRIEF DESCRIPTION OF THE DRAWINGS

FIG. 1 is a plan view of a substantially rectangular disposable diaper prior to being prefolded in accordance with this invention and includes elements broken away to show details of construction;

FIG. 2 is a plan view of the disposable diaper of FIG. 1 after it has been partially prefolded in accordance with this invention;

FIG. 3 is a plan view of the disposable diaper after it has been further prefolded in accordance with this invention; and FIG. 4 is a plan view of the disposable diaper showing its complete prefolded configuration for packaging.

DESCRIPTION OF THE PREFERRED EMBODIMENT OF THE INVENTION

Referring to FIG. 1 a disposable diaper 10, prior to being prefolded according to this invention, is substantially rectangular in plan view, and includes a longitudinal dimension defined by opposed end margins 12 and 14 and a shorter transverse dimension defined by opposed side margins 16 and 18. The diaper shown in FIG. 1 includes a moisture-pervious facing layer 20, an absorbent inner core 22 and a moisture-impervious backing layer 24. The specific components of the disposable diaper 10 shown in FIG. 1 are for purposes of illustration only, and are well known to people skilled in the art. The disposable diaper 10 can include many different combinations of elements therein. The present invention relates specifically to the prefolded configuration of a disposable diaper which has a substantially rectangular configuration in plan view when in an unfolded condition.

Referring to FIG. 3, each side of the prefolded disposable diaper 10 includes a double-pleat fold 26 including an inner panel 28 and an outer panel 30. If desired, the inner panels can be tacked at 31 by any suitable adhesive to retain them in a folded condition. Each outer panel 30 includes two wing sections 32 and 34; one on each side of a transversely extendng medial line 36. The wing sections 32, which are disposed on one side of the transversely extending medial line 36, diverge in a direction from said medial line to end margin 12 of the disposable diaper 10. The wing sections 34, which are disposed on the opposite side of the medial line 36, diverge in a direction from said medial line to end margin 14 of the disposable diaper 10.

Referring to FIG. 4, the prefolded construction of the disposable diaper 10 is completed by folding the diaper in half along the transversely extending medial line 36 is indicated by arrow 37. In the completely prefolded construction each wing section 32 and 34 extends outwardly beyond its underlying inner panel, whereby the diaper has a substantially flared configuration in plan view, being narrower adjacent the medial fold line 36 than adjacent the end margins 12 and 14 (only one end margin 12 being shown in FIG. 4). The disposable diaper shown in FIG. 4 is considered "baby-shaped" and provides a visible indication to a person placing the diaper on a wearer that the double-pleat folds 26 should not be removed.

Referring to FIGS. 1 and 2, the double-pleat folds 26 are formed by folding side sections 38 and 40 of the disposable diaper 10 along longitudinally extending fold lines 42 and 44, as indicated by arrows 45 and 47, to form inwardly directed flaps 46 and 48 which overlie a central section 50 of the diaper. Each of the inwardly directed flaps 46 and 48 is folded back upon itself along angled fold lines 52 and 54 to form the outer panels 30, each of which includes the two wing sections 32 and 34 (FIG. 3).

Referring to FIG. 2, the angled fold lines 52 and 54 along which the inwardly directed flap 46 is folded are disposed at an acute angle α to the longitudinal axis 56 of the disposable diaper, and intersect the junction of the longitudinally extending fold line 42 and the end margins 12 and 14, respectively. Likewise, the angled fold lines 52 and 54 along which the inwardly directed flap 48 is folded are disposed at an acute angle to the longitudinally extending axis 56 of the diaper, and intersect the junction of the longitudinally extending fold line 44 and the end margins 12 and 14, respectively. If desired, the acute angle α can be reduced so that the angled fold lines will intersect an end margin of the diaper intermediate the longitudinally extending boundaries of the flap which is folded.

To use the prefolded and packaged diaper 10 it is removed from the package and unfolded along the transversely extending medial line 36. In this condition the diaper 10 is ready to be placed upon a wearer without any requirement for the user to perform any difficult folding operations, i.e. the double-pleat folds remain intact, moreover the substantially flared configuration of the prefolded and packaged diaper provides a visible indication to a user that the double-pleat folds should not be removed from the diaper during application thereof about the torso of a wearer.

Having described my invention, I claim:

1. A prefolded and packaged disposable diaper which, in an unfolded condition, has a substantially rectangular configuration including a longitudinal dimension defined between end margins and a shorter transverse dimension defined between side margins, said prefolded and packaged diaper including:
   A. a double-pleat fold on each side of the diaper; each double-pleat fold including an inner panel overlying a central section of the diaper and an outer panel overlying said inner panel, each outer panel including two wing sections extending outwardly beyond its underlying inner panel, one of said wing sections being disposed on each side of a transversely extending medial line of the diaper; the wing sections of both outer panels which are disposed on the same side of the transversely extending medial line diverging from each other in a direction from the transversely extending medial line to an end margin of said diaper; and
   B. said disposable diaper being folded upon itself along the transversely extending medial line to dispose the wing sections of each outer panel in engagement with each other.

2. The prefolded and packaged disposable diaper according to claim 1, wherein the inner panels of both double-pleat folds extend for substantially the full longitudinal extent of the diaper.

3. The prefolded and packaged disposable diaper according to claim 1, wherein each inner panel is adhesively tacked to the central section of the diaper.

4. A prefolded and packaged disposable diaper which, in an unfolded condition, has a substantially rectangular configuration including a longitudinal dimension defined between end margins and a shorter transverse dimension defined between side margins, said prefolded and packaged diaper including:
   A. a double-pleat fold on each side of the diaper; each double-pleat fold including an inner panel and an outer panel overlying the inner panel, each inner panel extending for the full longitudinal extent of the diaper and having a transverse dimension defined between an outer longitudinally extending fold line which is substantially parallel to the longitudinally extending axis of the diaper and a pair of inner angled fold lines, each of said angled fold lines diverging away from the longitudinal axis of the diaper in a direction from the center of the diaper to an end margin of said diaper, each outer panel including two wing sections extending outwardly beyond its underlying inner panel, each wing section having a transverse dimension defined between one of said angled fold lines and a side margin of the diaper; and
   B. said disposable diaper being folded upon itself along a transversely extending medial line for disposing the wing sections of each outer panel in engagement with each other.

5. The prefolded and packaged disposable diaper according to claim 4, wherein each inner panel overlies a central section of the diaper and is adhesively tacked thereto.

* * * * *